United States Patent
Leung et al.

(10) Patent No.: US 11,730,352 B2
(45) Date of Patent: Aug. 22, 2023

(54) AUTO-EXPOSURE METHOD FOR WIRELESS CAPSULE ENDOSCOPE

(71) Applicant: Hong Kong Applied Science and Technology Research Institute Company Limited, Hong Kong (HK)

(72) Inventors: Chi Chung Leung, Hong Kong (HK); Hanqiang Huang, Shenzhen (CN)

(73) Assignee: Hong Kong Applied Science and Technology Research Institute Company Limited, Hong Kong (HK)

( * ) Notice: Subject to any disclaimer, the term of this patent is extended or adjusted under 35 U.S.C. 154(b) by 279 days.

(21) Appl. No.: 17/148,552

(22) Filed: Jan. 13, 2021

(65) Prior Publication Data

US 2022/0218188 A1    Jul. 14, 2022

(51) Int. Cl.
*A61B 1/04*         (2006.01)
*A61B 1/00*         (2006.01)
(Continued)

(52) U.S. Cl.
CPC .......... *A61B 1/041* (2013.01); *A61B 1/00016* (2013.01); *A61B 1/045* (2013.01); *A61B 1/273* (2013.01); *A61B 1/31* (2013.01)

(58) Field of Classification Search
CPC ..... A61B 1/041; A61B 1/00016; A61B 1/045; A61B 1/273; A61B 1/31; A61B 1/000095; A61B 1/0655
See application file for complete search history.

(56) References Cited

U.S. PATENT DOCUMENTS

| | | | |
|---|---|---|---|
| 7,605,852 B2 | 10/2009 | Olsen et al. | |
| 7,796,870 B2 | 9/2010 | Wang | |

(Continued)

FOREIGN PATENT DOCUMENTS

| | | |
|---|---|---|
| CN | 104203068 A | 12/2014 |
| CN | 105827990 A | 8/2016 |

(Continued)

OTHER PUBLICATIONS

"Medical Image Segmentation Based on Mixed Context CNN Model", U.S. Appl. No. 16/538,923, filed Aug. 13, 2019.

(Continued)

*Primary Examiner* — John P Leubecker
*Assistant Examiner* — Li-Ting Song
(74) *Attorney, Agent, or Firm* — Idea Intellectual Limited; Margaret A. Burke; Sam T. Yip

(57) ABSTRACT

A method for image-capturing of an internal organ by a miniature imaging device, comprising: generating a light at a first light intensity on to a subject area of an internal organ and capturing an image of the subject area by a miniature imaging device configured under default exposure parameter values; computing a second light intensity and optimized exposure parameter values based on brightness of the captured image, an orientation, a position, and a motion of the miniature imaging device; and generating a light at the second light intensity on to the subject area and recapturing the image of the subject area by the miniature imaging device configured under the optimized exposure parameter values. The second light intensity and optimized exposure parameter values are derived by an ex vivo processing unit in wireless data communication with the miniature imaging device.

18 Claims, 14 Drawing Sheets

(51) Int. Cl.
  *A61B 1/045* (2006.01)
  *A61B 1/273* (2006.01)
  *A61B 1/31* (2006.01)

(56) References Cited

U.S. PATENT DOCUMENTS

| | | | |
|---|---|---|---|
| 10,108,845 B2 | 10/2018 | Wu et al. | |
| 10,354,122 B1 | 7/2019 | He et al. | |
| 10,586,336 B2 | 3/2020 | Hu et al. | |
| 2004/0242962 A1* | 12/2004 | Uchiyama | A61B 1/0002 600/109 |
| 2007/0052839 A1 | 3/2007 | Kong et al. | |
| 2007/0225560 A1* | 9/2007 | Avni | A61B 1/000095 600/118 |
| 2013/0314518 A1 | 11/2013 | Mitsuhashi | |
| 2014/0155709 A1* | 6/2014 | Ikai | A61B 1/00158 600/302 |
| 2017/0366724 A1 | 12/2017 | Murakita | |
| 2018/0243043 A1 | 8/2018 | Michihata et al. | |
| 2020/0337533 A1* | 10/2020 | Wang | A61G 13/04 |
| 2022/0012915 A1* | 1/2022 | He | A61B 1/045 |

FOREIGN PATENT DOCUMENTS

| | | |
|---|---|---|
| CN | 105939451 A | 9/2016 |
| CN | 110477844 A | 11/2019 |
| CN | 110830731 A | 2/2020 |
| CN | 111182232 A | 5/2020 |
| CN | 111343387 A | 6/2020 |
| CN | 111343389 A | 6/2020 |
| CN | 111726506 A | 9/2020 |
| EP | 1627592 A1 | 2/2006 |
| EP | 2633798 A1 | 9/2013 |
| JP | 2006305322 A | 11/2006 |

OTHER PUBLICATIONS

"Method for Medical Image Segmentation using Convolutional Neural Network", U.S. Appl. No. 16/785,784, filed Feb. 10, 2020.
International Search Report and Written Opinion of corresponding PCT Patent Application No. PCT/CN2021/073218 dated Sep. 28, 2021.
First Office Action of corresponding China patent application No. 202180000470.6 dated Apr. 12, 2023.

* cited by examiner

AUTO-EXPOSURE METHOD FOR WIRELESS CAPSULE ENDOSCOPE

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention generally relates to the field of imaging in medicine. More specifically, the present invention relates to methods and apparatuses for image-capturing of internal organs of humans and animals.

BACKGROUND OF THE INVENTION

Endoscopes are widely used in the medical and industrial fields. The internal areas within the human body that an endoscope can be used in include the gastrointestinal tract, such as the esophagus, stomach, duodenum, small intestine, large intestine, rectum and colon; the respiratory tract, such as the nasal cavity, throat and lower respiratory tract; the urinary tract, such as the urethra, bladder, ureter, renal pelvis and kidney; the female reproductive system, such as the vagina, cervix and uterus; the abdominal cavity; joint cavity; thoracic cavity; etc. With the advancement of technology, the diagnostic use of endoscopes is vast.

The use of a traditional endoscope includes extending a slender optical lens into a patient's body through a slender tube, so that an operator can observe the internal organ. Such technique allows the tube to be inserted only through an open cavity of the human body. For example, a gastroscope is inserted through a patient's mouth, and a cystoscope is inserted through a patient's urethral. However, some organs do not have open cavities for which traditional endoscopes can be used in.

In recent years, capsule endoscopes have been introduced, which are non-invasive inspection methods. A capsule endoscope usually contains a lighting mechanism that illuminates the target internal organ area, a miniature camera that takes images, along with a battery and an image sensor. After the patient swallows the capsule, the condition of the entire digestive tract can be observed as the capsule travels through the gastrointestinal tract. While the capsule moves through the tract, the camera continuously captures images until the battery is exhausted, and then it is excreted from the body via urination and/or defecation. Thus, enabling the doctors to diagnose diseases in the gastrointestinal tract using the images taken by the capsule endoscope. However, the limitation is that the battery capacity of the capsule endoscope is extremely limited and the images are captured without much control, often resulting in poor picture quality, missing information, and too few pictures of the concerned area.

Wireless capsule endoscopy is another method of taking images of the digestive tract by using a wireless capsule with a miniature camera and LED. The captured images are transmitted to an external recorder via a wireless link, and then the images are sent to a computer workstation for further post-processing and viewing. At present, wireless capsule endoscopy has been designed to have the functions of active locomotion and localization, which can be controlled by manipulation via magnetic force exerted by an ex vivo magnetic inducing module or electro-mechanical mechanism in radio frequency (RF) signal communication with an external control module.

Japan Patent Application No. 2006305322A discloses a capsule endoscope system, which is capable of obtaining an appropriate exposure value in an imaging device without inserting other devices in a capsule endoscope. The operation method of the capsule endoscope system when photographing the subject's digestive tract is also provided. First, a subject wearing an extracorporeal unit swallows the capsule endoscope whose power is turned on by activating a power switch circuit and moves it to the stomach. At this time, a controller instructs a driver to supply a current to a light emitting diode at a predetermined initial value when power is turned on. The driver supplies an initial value of current to the light emitting diode, so that it emits light. An image sensor then images the body cavity illuminated by the illumination light emitted from the light emitting diode.

U.S. Patent Application Publication No. 2013/0314518A1 discloses a sequencing process of images captured by the capsule endoscope. A pre-exposure process (i.e. $1^{st}$ image) of performing exposure in advance is performed before the main exposure process (i.e. $2^{nd}$ image) is performed to acquire an actual image under the control of a control unit.

China Patent Application Publication No. 110477844A discloses an apparatus for judging the peak brightness value of the images to be within the scope of predetermined luminance values, and a method for avoiding overexposure of collected pictures is also provided. The method includes acquiring images, performing a luminance analysis processing on collected images, and determining the peak brightness value of the images.

However, all methods in the aforementioned prior art do not consider the orientation, position, or movement of the wireless capsule endoscope within the organ interior, which can significantly affect the exposure of the images. For example, in a stomach inspection, inside the relatively large stomach cavity, the capsule may move rapidly under the control of an ex vivo magnetic inducing module and the lighting conditions change substantially from one position to another, resulting in many underexposed or overexposed images. This in turn limits the number of useful images that can be captured by the capsule endoscope, which has a very limited battery capacity.

Therefore, in view of the shortcomings of the existing wireless capsule endoscopy, there is a need in the art to provide a way to calculate the optimal luminous level for every position and rotation of the capsule within an organ interior.

SUMMARY OF THE INVENTION

To address the above-mentioned shortcomings, the present invention provides an efficient auto-exposure (AE) method through off-loading the AE computation process to an ex vivo processing unit, which combines the capsule orientation, position, and motion data and image brightness information to obtain the desired exposure parameter values and camera light intensity.

Because the present invention requires the in vivo capsule to capture only one trial image for calibration for finding the desirable exposure, and that the calibration computation can be offloaded to the ex vivo processing unit, the present invention reduces the miniature imaging device's battery power consumption and increases the efficiency of the wireless capsule endoscopy procedure.

In accordance to one aspect of the present invention, the present invention provides a method for image-capturing of an internal organ, comprising generating a light at a first light intensity on to an area of an internal organ interior and capturing a first image of that area by a miniature imaging device under default exposure parameter values; determining a second light intensity and computing optimized exposure parameter values associated with the second light intensity based on the brightness of the captured first image and the orientation, position, and motion of the miniature imaging device at which the first image is captured; and generating a light at the second light intensity on to the same area of the internal organ and recapturing a second image of that area by the miniature imaging device under the optimized exposure parameter values. In one embodiment, the computation of the optimized exposure parameter values are performed by an ex vivo processing unit in wireless data communication with the miniature imaging device, and the computed optimized exposure parameter values are subsequently transmitted to the miniature imaging device.

In accordance to one embodiment, the computation of the second light intensity and optimized exposure parameter values comprises an auto-exposure (AE) process performed by an AE engine module in the ex vivo processing unit using the miniature imaging device's orientation, position and motion; and a luma of the first image to determine the optimized camera light intensity (e.g. LED brightness level) and image sensor (e.g. CMOS sensor) exposure parameter values.

In accordance to one embodiment, the obtainment of the position and motion of the miniature imaging device comprises receiving control data of an ex vivo magnetic inducing module that is in remote magnetic manipulation of the miniature imaging device; and estimating the position and motion of the miniature imaging device from the control data. The obtainment of the orientation of the miniature imaging device comprises receiving measurement data from an inertial measurement unity (IMU) in the miniature imaging device.

In accordance to yet another embodiment, the computation of the luma of the first image includes dividing the first image into a plurality of image zones; and comparing a brightness level of each of the image zones with an average brightness of the plurality of image zones to determine at least one of underexposure and overexposure conditions of the first image.

In accordance to one embodiment, the computation of the luma of the first image further includes assigning a weighting factor to the luma of each of the plurality of image zones after dividing the first captured image into the plurality of image zones.

In accordance to one embodiment, the image zones are constructed as i×j uniform squares, and wherein i is a positive integer in a range of 1 to 6, and j is a positive integer in a range of 1 to 6.

In accordance to one embodiment, the computation of the luma of the first image further includes calculating an average luma value L of the image zones; if L<target luma—tolerance value (e.g. 15), the first image is determined to be taken under an underexposed condition; and if L>target luma+tolerance value (e.g. 15), the first image is determined to be taken under an overexposed condition; if the first image is underexposed, calculating an average luma value rL of three to five image regions in the first image with the lowest luma values; if the camera of the miniature imaging device faces away from the organ interior wall at a pitch angle of approximately 40 to 50 degree and spins, or the miniature imaging device moves away from the organ interior wall, setting the optimized exposure parameters to predefined exposure parameter values and increasing the light intensity by a luma D, wherein D is obtained according to the equation: D=|target luma−(rL)|; and if the miniature imaging device is stationary, increasing the light intensity by D; else if the first image is overexposed, calculating an average luma value rL of three to five image regions with the highest luma values; if the miniature imaging device moves sideways along the organ interior wall, setting a predefined light intensity and optimized exposure parameters to predefined exposure parameter values tuned for overexposure condition; if the camera of the miniature imaging device faces away from the organ interior wall at a pitch angle of approximately 40 to 50 degree and spins, or the miniature imaging device moves toward the organ interior wall, setting the optimized exposure parameter to predefined exposure parameter values and decreasing the light intensity by a luma D, wherein D is obtained according to the equation: D=|target luma−(rL)|; and if the miniature imaging device is stationary, decreasing the light intensity by D.

In accordance to one embodiment, if the first image is not either underexposed or overexposed, grouping one or more of the image zones into a region of interest (ROI) according to the luma values of the plurality of image zones; and calculating a group luma gL of the ROI. Further, if gL>target luma+tolerance value (e.g. 15), the first image is determined to be taken under an overexposed condition.

BRIEF DESCRIPTION OF THE DRAWINGS

Embodiments of the invention are described in more details hereinafter with reference to the drawings, in which:

Figures 5D, 5E, 5F:
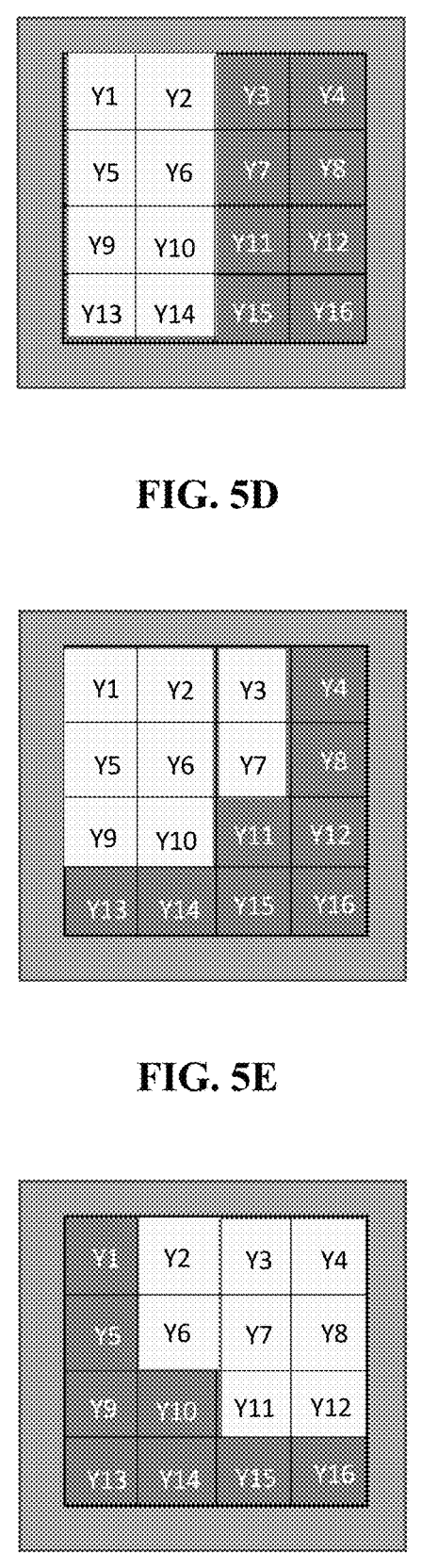
Figures 5G, 5H:
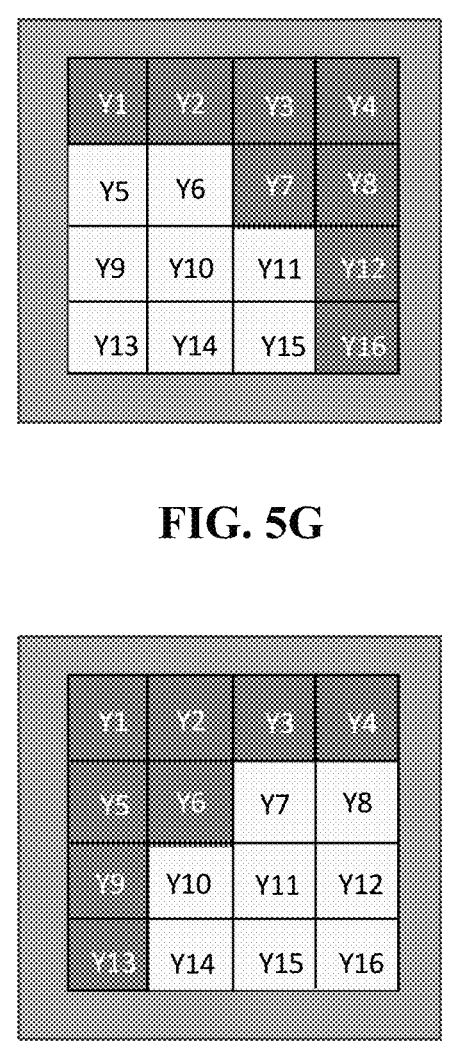

FIGS. 5A-5H illustrate the luma of a group of eight image zones having different arrangements.

DETAILED DESCRIPTION

In the following description, apparatuses and methods of auto-exposure for capsule endoscopes and the likes are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

In a wireless capsule endoscopy procedure for an internal organ, such as the stomach, active locomotion control is required to maneuver the capsule to image the entire stomach wall during stomach inspection. A magnetic control system, such as one having an ex vivo magnetic inducing module with localization and a navigation module, is commonly used. Generally, the image sensor in a capsule has a build-in AE engine that can work with a driver software to iteratively capture six to seven image frames to achieve the desired exposure. However, due to the limited battery power capacity, the imaging frame rate of the capsule endoscope is only two to four frame per second. In other words, the built-in auto-exposure response time is relatively slow, about 1.5 to 3.5 seconds. In order to improve the exposure condition of the images and reduce the battery power consumption rate, the present invention provides a number of methods for obtaining optimized images from a wireless capsule endoscope.

Figure 1:
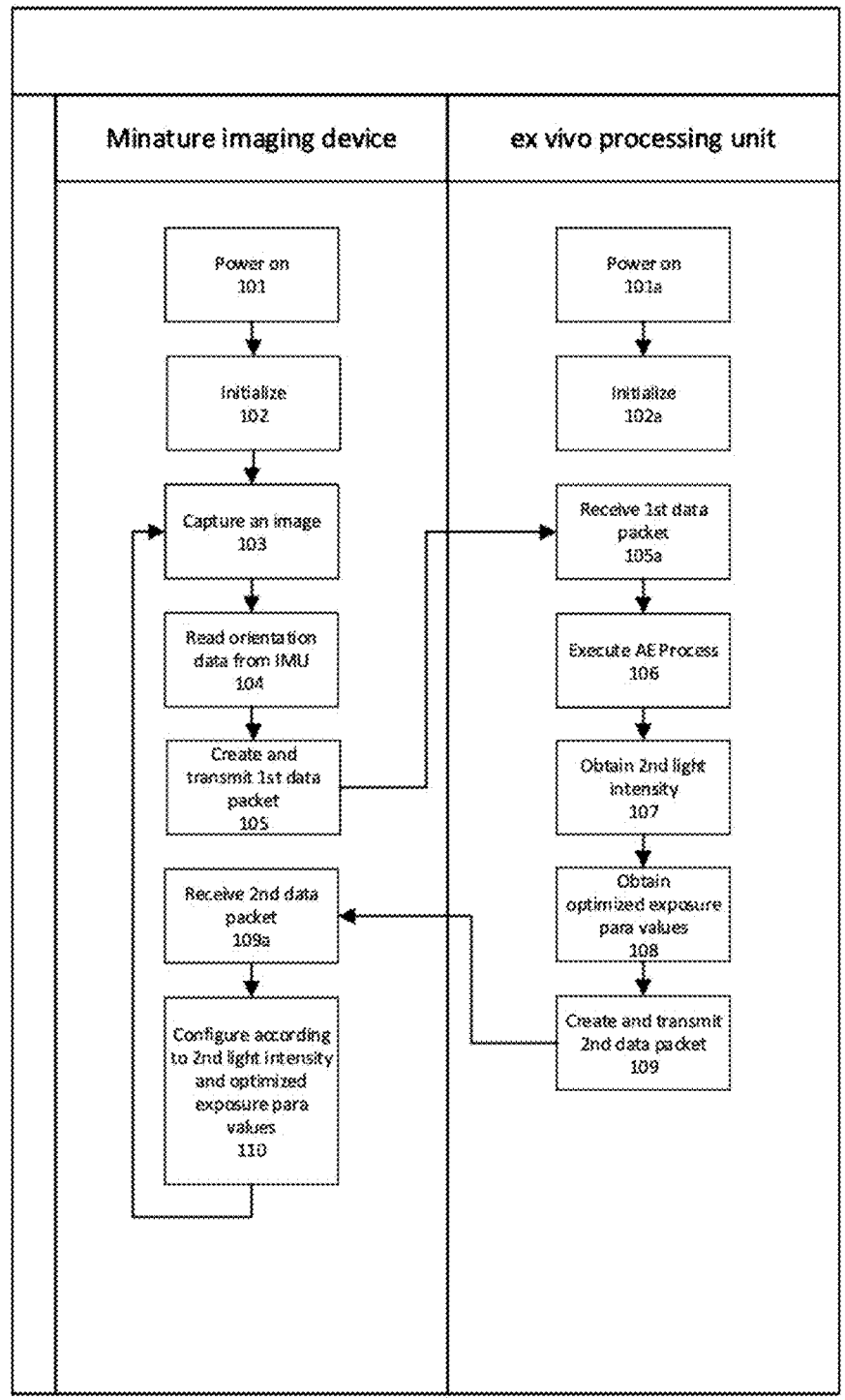
FIG. 1 depicts a schematic diagram of the overall process of capturing images by using a wireless capsule in accordance to various embodiments of the present invention.

Referring to FIG. 1. In accordance to one embodiment of the present invention, a method for image-capturing of an internal organ is provided, the method comprises the following process steps: First, (101) the power of the miniature imaging device is turned on, and (101A) the power of the ex vivo processing unit is turned on; (102) the miniature imaging device is initialized with the set of default exposure parameter values, and (102A) the ex vivo processing unit is initialized. Next, (103) an image of an area of the internal organ interior is captured; (104) data of the orientation of the miniature imaging device from an inertial measurement unit (IMU) in the miniature imaging device is collected, and then (105) a first data packet, containing the image and the inertial measurement data, is created and wirelessly transmitted to the ex vivo processing unit. After (105A) receiving the first data packet, (106) an AE process is executed by an AE engine module of the ex vivo processing unit. Next, (107) a second light intensity is determined based on the brightness of the captured image and orientation, position, and motion of the miniature imaging device; and (108) optimized exposure parameter values associated with the second light intensity are obtained. Next, (109) a second data packet, containing the second light intensity value and the optimized exposure parameter values, is wirelessly transmitted back to the miniature imaging device, and (109A) the miniature imaging device receives the second data packet. Lastly, (110) with the miniature imaging device configured according to the second light intensity value and the optimized exposure parameter values, the process loops back to step 103 to recapture the image of the area of the internal organ interior under the second light intensity value and the optimized exposure parameter values. The image-recaptured is wirelessly transmitted back to the ex vivo processing unit and optionally displayed on an external imaging equipment, thereby allowing a medical practitioner to diagnose the internal organ.

In one embodiment, the miniature imaging device is a wireless capsule, which includes one or more, preferably at least four, light-emitting diode (LEDs) for lighting, a camera, a battery power supply, an inertial measurement unit (IMU), and a CMOS image sensor for imaging sensing; the ex vivo processing unit is a portable recorder.

Figure 2A:
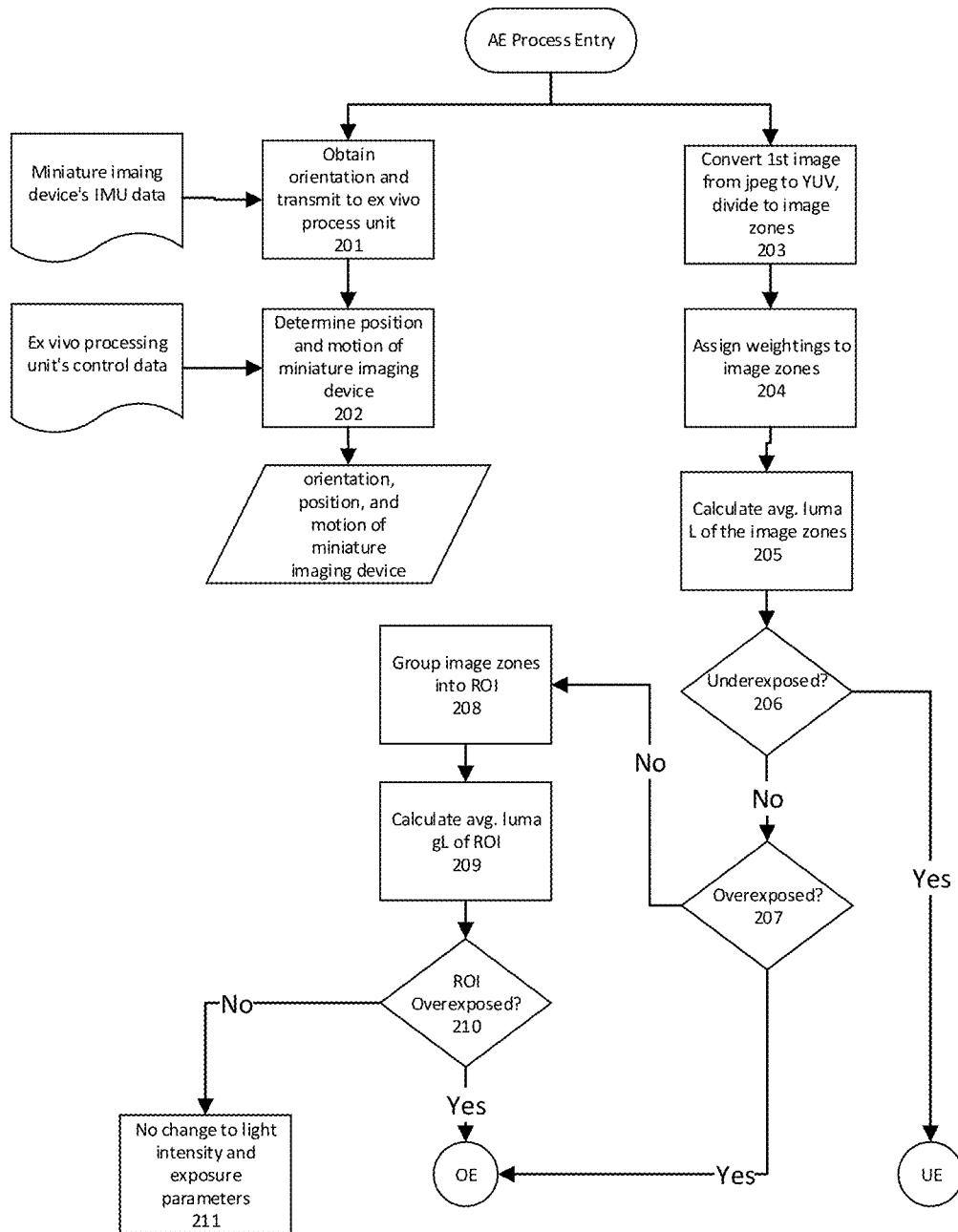
FIGS. 2A and 2B depict a schematic diagram of the overall process of using an auto-exposure (AE) engine module to calculate the camera light intensity and image sensor exposure parameter values.
Figure 2B:
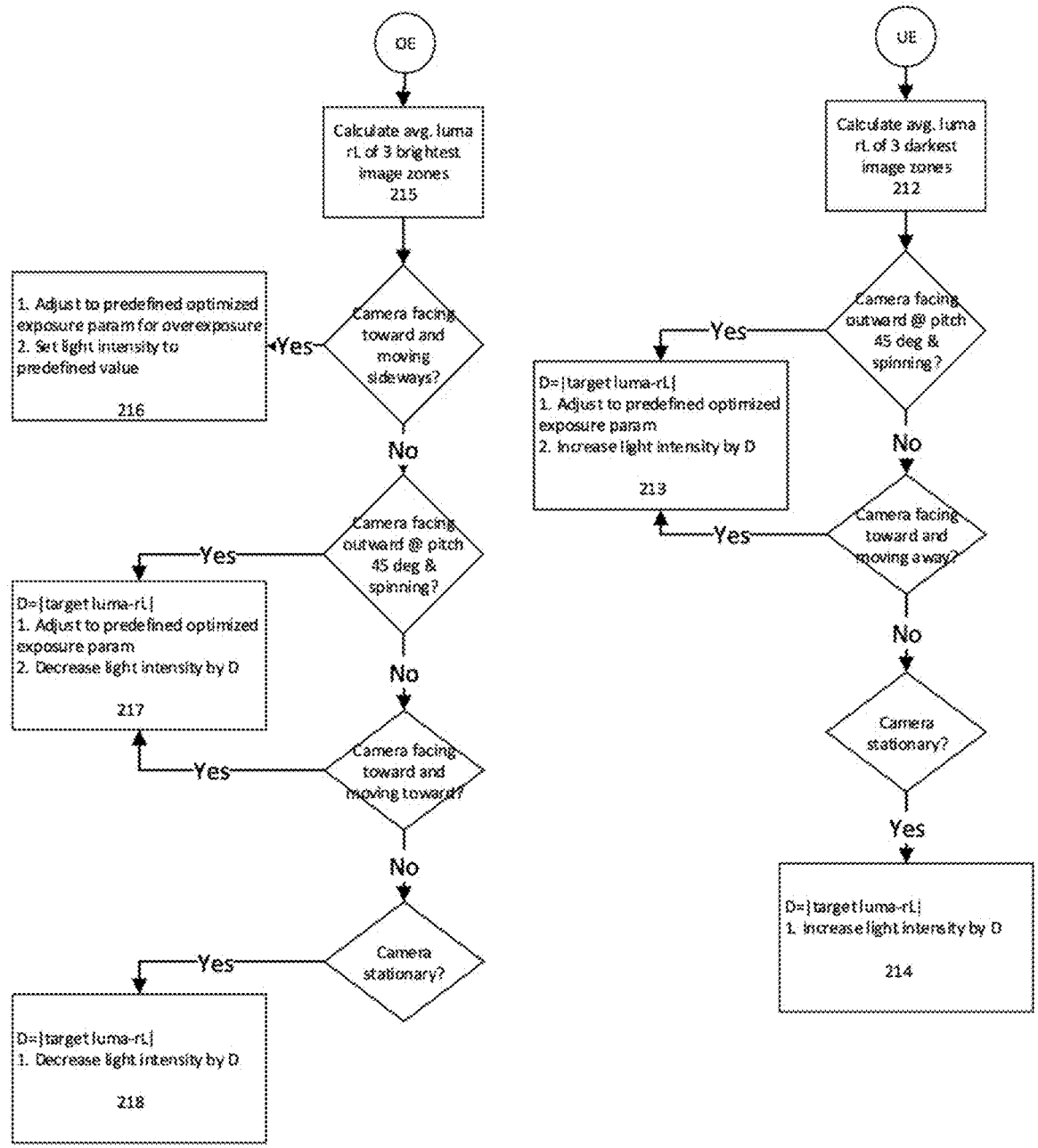

Referring to FIGS. 2a and 2b. In accordance to one embodiment, the AE process is performed by an AE engine module of the ex vivo processing unit. The AE process uses the orientation, position, and motion of the miniature imaging device and the luma of the first image-captured to calculate the optimal light intensity and exposure parameter values for correct exposure.

In one embodiment, (201) the orientation of the miniature imaging device, and in turn the pitch angle of the miniature imaging device's camera, is obtained from the IMU data and transmitted wirelessly from the miniature imaging device to the ex vivo processing unit; (202) the position and motion of the miniature imaging device are obtained from the control data of the ex vivo magnetic inducing module in magnetic manipulation of the miniature imaging device, wherein the control data may be transmitted from the ex vivo magnetic inducing module to the ex vivo processing unit via wired or wireless data communication.

Figure 3A:
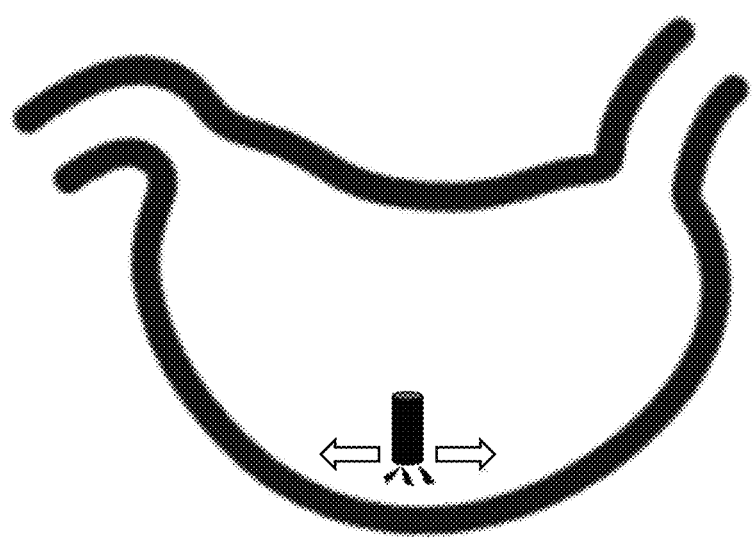
FIG. 3A illustrates a capsule with a camera closely facing the stomach wall and moving sideways along the wall.
Figure 3B:
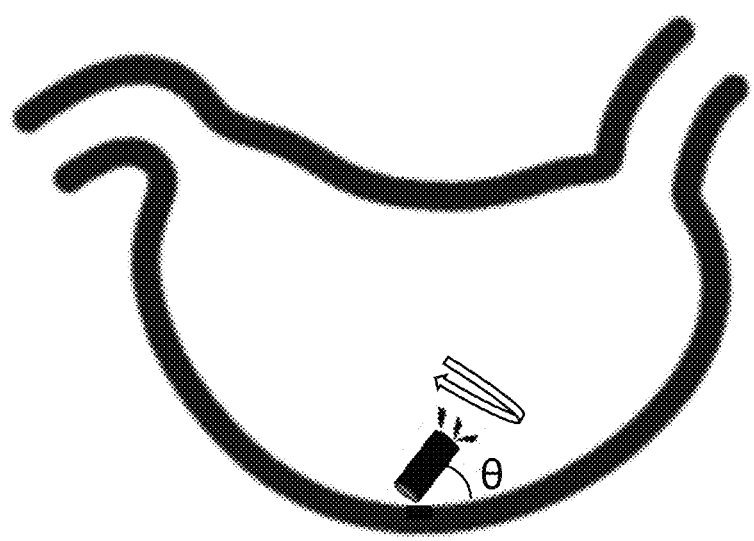
FIG. 3B illustrates a capsule with a camera facing away from the stomach wall with a pitch angle, θ, and spinning slowly.
Figure 3C:
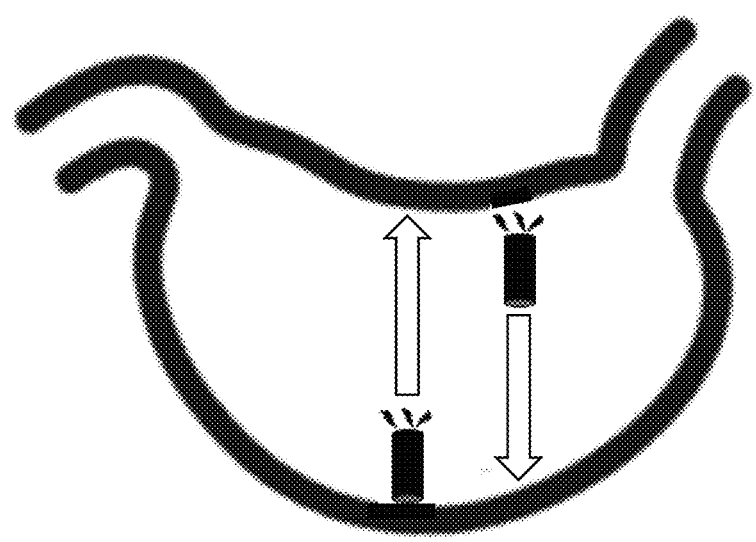
FIG. 3C illustrates a capsule with a camera moving towards or away from the stomach wall.

In one embodiment, the combinations of orientations, positions, and motions of the miniature imaging device are classified into three categories: 1.) with its camera closely facing toward the organ interior wall the miniature imaging device is moving sideways along the organ interior wall, as shown in FIG. 3a; 2.) the camera of the miniature imaging device is facing away from the organ interior wall and at a pitch angle of approximately 40-50 degree and the miniature imaging device is spinning in circle, as shown in FIG. 3B; and 3.) with its camera facing toward the organ interior wall the miniature imaging device is moving toward or away from the organ interior wall, as shown in FIG. 3C.

In one embodiment, the AE process comprises: (203) converting the first image from JPEG format to YUV format and dividing into a plurality of image zones, but ignoring the rim of the first image; (204) assigning a weighting factor to the brightness of each of the plurality of image zones; (205) calculating an average luma value L of the weighted image zones; (206) determining if the first image is underexposed such that L<target luma−K; and (207) determining if the first image is in an overexposed condition such that L>target luma+K; wherein K is a tolerance value for debouncing purpose; and K is set to 15, which is a preferred value based on observations in a number of experiments with the embodiments of the present invention. Other values are possible under other usage conditions and applications of the embodiments of the present invention.

Figure 4:
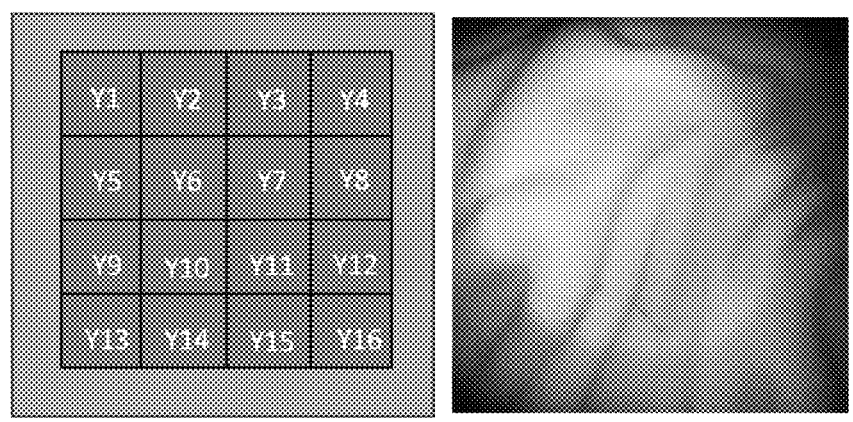
FIG. 4 illustrates an image divided into 16 image zones in accordance with one embodiment of the present invention.
Figure 5A:
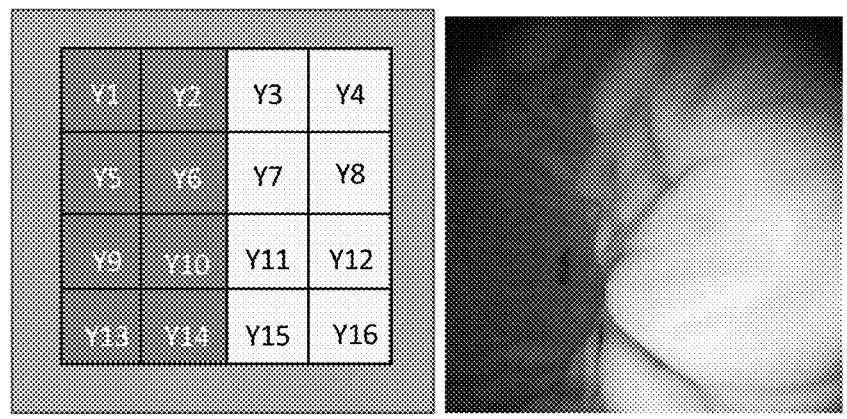
Figure 5B:
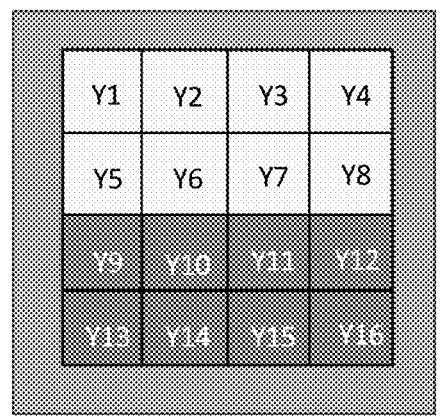
Figure 5C:
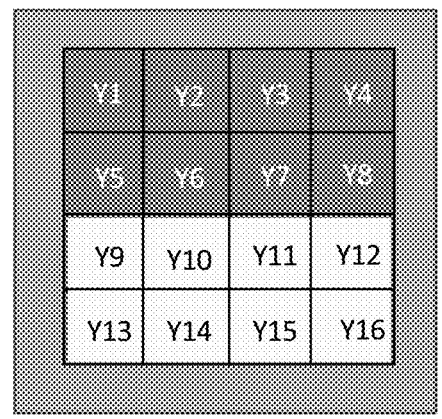

In one embodiment, the image zones are constructed as i×j uniform squares, and i is a positive integer in a range of 1 to m, and j is a positive integer in a range of 1 to n. For example, i×j uniform squares may be a 4×4 pattern (e.g. as shown in FIG. 4, a 5×5 pattern, a 4×5 pattern, etc.) m and n are preferably 6 based on observations in a number of experiments with the embodiments of the present invention. Other values are possible under other usage conditions and applications of the embodiments of the present invention. An ordinarily skilled person in the art will appreciate that other patterns for the arrangement of the image zones, such as uniform triangles, hexagons, and other polygons, are possible and readily adoptable without undue experimentation and deviation from the spirit of the present invention.

Since the field of view (FOV) of the camera is only about 130 degree, the orientation of the miniature imaging device affects the captured image, which may cause some portions to be overexposed and others underexposed in the same image. Referring to FIG. 2A again. The AE process further comprises: if target luma−tolerance value<L<target luma+tolerance value, that is the first image being neither underexposed nor overexposed, (208) grouping two or more of the image zones according to their lumas into a region of interest (ROI); (209) calculating a group luma gL of the ROI image zones of the first image; and (210) determining if the first image is overexposed, wherein if gL>target luma+K, the first image is determined to be overexposed. If gL≤target luma+K, then (211) no change is to be made to the light intensity and the exposure parameter values. Again, K is a tolerance value for debouncing purpose; and K is set to 15, which is a preferred value based on observations in a number of experiments with the embodiments of the present invention. Other values are possible under other usage conditions and applications of the embodiments of the present invention.

The group luma gL of the ROI image zones of the first image is used for detecting any overexposure in the ROI. The gL is calculated according to the following equation:

$$gL = \frac{\sum Y_i}{n};$$

where $Y_i$ is the luma of image zone i and n is the number of image zones in the ROI included in the calculation. To illustrate, FIGS. 5A-5H show the different possible image zone 4×4 patterns where n is 8 and i∈{3,4,7,8,11,12,15,16}, {1,2,3,4,5,6,7,8}, {9,10,11,12,13,14,15,16}, {1,2,5,6,9,10,13,14}, {1,2,3,5,6,7,9,10}, {2,3,4,6,7,8,11,12}, {5,6,9,10,11,13,14,15}, and {7,8,10,11,12,14,15,16} respectively.

From the observations in a number of experiments with the embodiments of the present invention, the ROI image zones are usually found in the bright image zones near the edges or corners in the first image having one of a bright left transitioning to dark right pattern, a bright right transitioning to dark left pattern, a bright top transitioning to dark bottom pattern, a bright bottom transitioning to dark top pattern, a bright corner transitioning to dark opposite corner pattern, or a center bright center transitioning to dark perimeter pattern.

Referring to FIG. 2B. The AE process further comprises: if the first image is determined to be underexposed, (212) calculating an average luma value rL of three image frames with the lowest luma values; if the camera of the miniature imaging device is facing away from the internal organ interior wall at a pitch angle of approximately 45 degree and the miniature imaging device is spinning, or if with its camera facing toward internal organ interior wall the miniature imaging device is moving away from the internal organ interior wall, (213) adjusting the exposure parameter values to a first set of predefined exposure parameter values and the camera light intensity be increased by a luma D, wherein D is obtained according to the equation:

$$D = |target\ luma - rL|;$$

where the target luma has a luma value representing the desired luma of the second image to be captured under the condition in which the first image was captured; else if the miniature imaging device is stationary, then (214) increasing the light intensity by D.

The AE process further comprises: if the first image is overexposed, (215) calculating an average luma value rL of three image frames with the highest luma values; if with its camera of the miniature imaging device is closely facing toward and moving sideways along the organ interior wall, (216) setting the light intensity to a predefined light intensity and the exposure parameter to predefined exposure parameter values tuned for overexposure condition (this is so because under such orientation and movement of the miniature imaging device, the lighting condition varied little); else if the camera of the miniature imaging device is facing away from the internal organ interior wall at a pitch angle of approximately 45 degree and the miniature imaging device is spinning in circle, or if the camera is facing toward the internal organ interior wall the miniature imaging device and is moving toward to the internal organ interior wall, (217) setting the exposure parameters to a second set of predefined exposure parameter values and decreasing the light intensity by a luma D, wherein D is obtained according to the equation:

$$D = |target\ luma - rL|;$$

where the target luma has a luma value representing the desired luma of the second image to be captured under the condition in which the first image was captured; else if the miniature imaging device is stationary, then (218) decreasing the light intensity by D.

In one embodiment, to change the light intensity, a miniature imaging device's LED brightness level is to be set, wherein the LED brightness level LED brightness level is determined by a lookup table cross-referencing LED brightness levels of the specific made, model, type, and configuration of the LED(s) of the miniature imaging device with desired lumas and distances between the image sensor and the object to be image-captured.

In one embodiment, the first and second sets of predefined exposure parameter values and the predefined exposure parameter values tuned for overexposure condition are obtained from a lookup table specific to the image sensor used in the miniature imaging device.

The internal organ may be the gastrointestinal tract such as, but not limited to, the esophagus, stomach, duodenum, small intestine, large intestine, rectum, and colon. The targeted subject may be a human person or an animal such as, but not limited to, a member of the feline, canine, equine, bovine, or ayes family.

The afore-described embodiments are further illustrated by way of exemplary implementations below.

Calculation of Average Luma Value

Example 1

As shown in FIG. 4, under an image zone 4×4 pattern, the image zones are referred to as $Y_1$ to $Y_{16}$ in an order from top left to bottom right. The central four image zones $Y_6$, $Y_7$, $Y_{10}$ and $Y_{11}$ each is having a weighting factor of 1.2, and the average luma L is calculated according to the following equation:

$$L = [(Y_6+Y_7+Y_{10}+Y_{11})\times 1.2+(Y_1+Y_2+Y_3+Y_4+Y_5+Y_8+Y_9+Y_{12}+Y_{13}+Y_{14}+Y_{15}+Y_{16})]/16$$

Different Capsule Positions and Motion Inside Stomach

Example 2

As shown in FIG. 3A, the camera of the capsule is closing facing the stomach wall, and is moving sideways along the stomach wall. Since the lighting conditions are almost constant, similar exposure performance is obtained by applying the methods according to the embodiments of the present invention.

Example 3

As shown in FIG. 3B, the camera of the capsule is facing outward at a pitch angle of 45 degree and the capsule is spinning in circle. The purpose of this orientation and motion is to take the stomach side wall images. By applying the methods according to the embodiments of the present invention, the resulting images are showing that the underexposure of the image edge wall improved.

Example 4

As shown in FIG. 3C, the capsule is moving toward and away from the stomach wall. By applying the methods according to the embodiments of the present invention, both underexposure and overexposure conditions have improved significantly.

Calculation of Capsule Pitch Angle

Example 5

Figure 6:
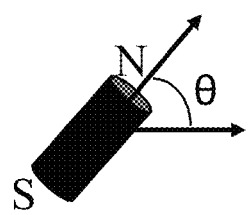
FIG. 6 depicts a schematic diagram of the north pole and south pole of magnet inside the capsule.

Referring to FIG. 6. When the driver magnet of the capsule rotates, the capsule pitch angle changes. The x, y, z components of an accelerometer inside the capsule's IMU are read to calculate the capsule pitch angle, θ. The pitch angle, θ, is calculated according to the following equation:

$$\tan^{-1}\theta = \frac{a_y}{a_x};$$

where $a_y$ is they component of the accelerometer; and $a_x$ is the x component of the accelerometer.

Figure 7A:
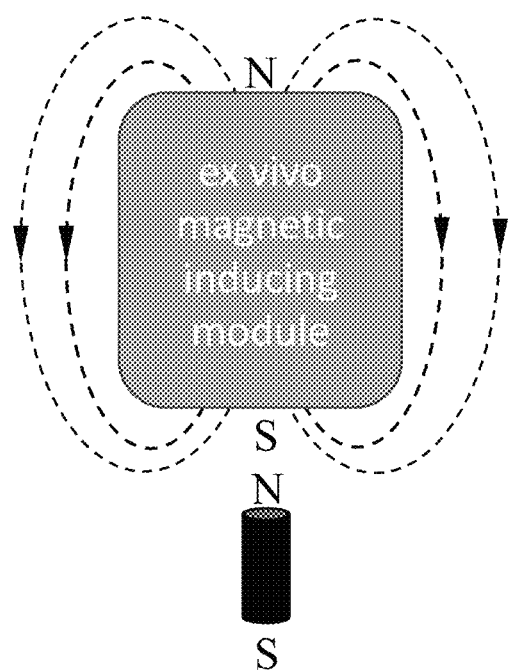
FIGS. 7A and 7B illustrate two situations of remote magnetic manipulation of a capsule in vitro by an ex vivo magnetic inducing module.
Figure 7B:
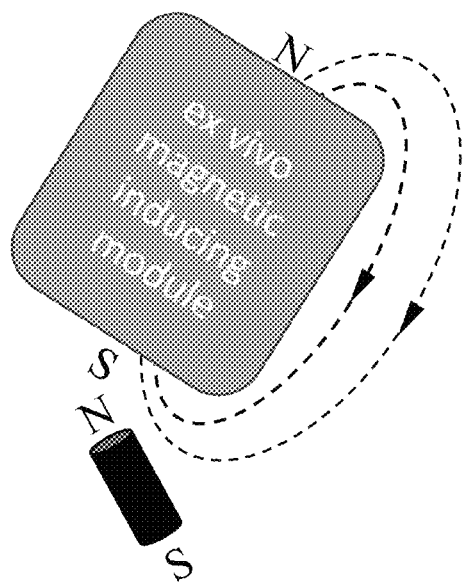

Assuming that the capsule moves slowly, the south pole of the driver magnet of the ex vivo magnetic inducing module aligns with the north pole of the driver magnet of the capsule, as shown in FIG. 7A. As shown in FIG. 7B, when the ex vivo magnetic inducing module causes its driver magnet to move in a circular motion, it induces the capsule to rotate accordingly. The capsule pitch angle θ can be in a range of 40-50 degree.

Capsule Up/Down Position Control

Example 6

Figure 8A:
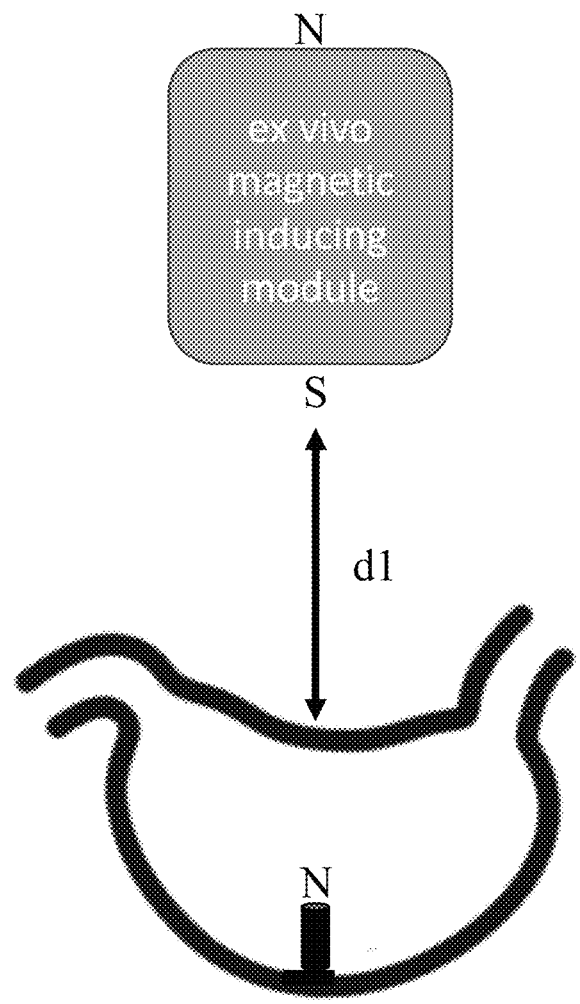
FIG. 8A shows the capsule located at the bottom of the stomach when the distance of an ex vivo magnetic inducing module is $d_1$.
Figure 8B:
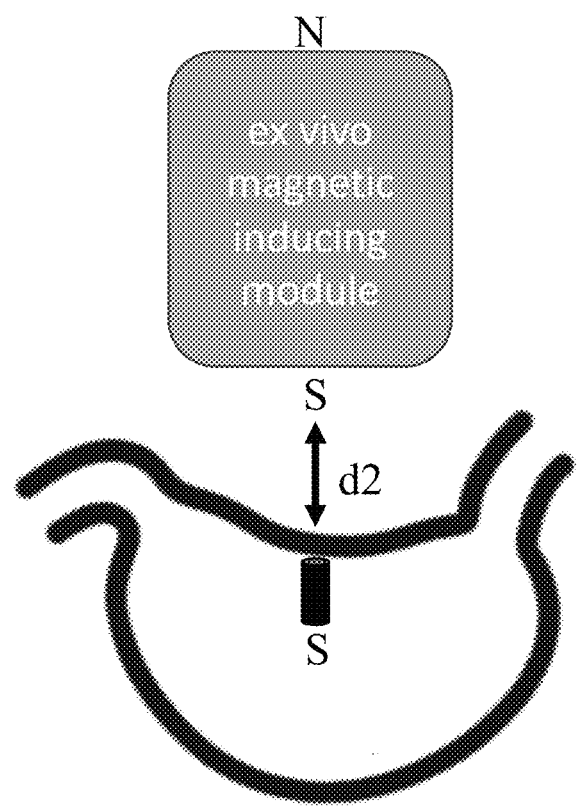
FIG. 8B shows the capsule is located at the top side of the stomach when the distance of an ex vivo magnetic inducing module is $d_2$.

In order to move the capsule up and down inside the stomach such that the distance between the driver magnet of the capsule and the stomach changes, a change in magnetic force exerted on to the driver magnet of the capsule is needed. As shown in FIG. 8A, a relatively large distance $d_1$ between the ex vivo magnetic inducing module and the capsule is causing a relatively weak magnetic force exerted on to the driver magnet of the capsule. When the force of gravity is stronger than the sum of the magnetic force and buoyancy of the capsule, the capsule sinks and moves in the direction away from the ex vivo magnetic inducing module. In the contrary, as shown in FIG. 8B, a relatively short distance $d_2$ between the ex vivo magnetic inducing module and the capsule is causing a relatively strong magnetic force exerted on to the driver magnet of the capsule. When the sum of the magnetic force and buoyancy of the capsule is stronger than the force of gravity, the capsule is pulled towards the ex vivo magnetic inducing module.

Adjustment of the LED Brightness Level

Example 7

Assuming that the capsule is in a dark environment in the stomach, and that in addition to front lighting conditions, no excess back lighting conditions may occur. The camera lighting of capsule includes at least four LEDs, which are controlled by pulse width modulation (PWM). The relation between the LED brightness and duty cycle of PWM is:

$$\text{brightness} \propto \frac{t \times c}{d};$$

where c is a predefine constant by calibration; t is the PWM duty cycle; and d is the distance between image sensor and target object.

In order to set the LED brightness level for the desire luma, the LED brightness level is adjusted according to Table 1 to map the value. For example, if the distance between image sensor and target object is about 1.5 cm and the current LED brightness level is at level 11, and the row of level 11 is iterated, and that the closest value to the current image luma would be found to be a133. In order to reduce the image luma by a delta luma D to a target image luma of a16, the 1.5 cm column is iterated until the target image luma of a16 is found. For example, for D=(a133−a16), LED brightness level 2 should be set.

TABLE 1

Image Luma Values for Different Distances Between the Image Sensor and Target Object and LED brightness levels

| | Luma value | | | | | | | | | | | | |
|---|---|---|---|---|---|---|---|---|---|---|---|---|---|
| | 0.5 cm | 1 cm | 1.5 cm | 2 cm | 2.5 cm | 3 cm | 3.5 cm | 4 cm | 4.5 cm | 5 cm | 6 cm | 6.5 cm | 7 cm |
| LED (level 1) | a1 | a2 | a3 | a4 | a5 | a6 | a7 | a8 | a9 | a10 | a11 | a12 | a13 |
| LED (level 2) | a14 | a15 | a16 | a17 | a18 | a19 | a20 | a21 | a22 | a23 | a24 | a25 | a26 |
| ... | | | | | | | | | | | | | |
| LED (level 11) | a131 | a132 | a133 | a134 | a135 | a136 | a137 | a138 | a139 | a140 | a141 | a142 | a143 |
| LED (level 12) | a144 | a145 | a146 | a147 | a148 | a149 | a150 | a151 | a152 | a153 | a154 | a155 | a156 |

The optimized exposure parameter values and digital sensor gain are calibrated and set to the CMOS image sensor before taking the real measurement.

Although the afore-described preferred embodiments provide that the AE process is executed by an AE engine module in an ex vivo processing unit, an ordinarily skilled person in the art will appreciate that AE process be executed by an AE engine module residing in the miniature imaging device (or the capsule endoscope) such that an ex vivo processing unit is not necessary.

The functional units and modules of the apparatuses and the methods in accordance to embodiments disclosed herein may be implemented using computing devices, computer processors, or electronic circuitries including but not limited to application specific integrated circuits (ASIC), field programmable gate arrays (FPGA), and other programmable logic devices configured or programmed according to the teachings of the present disclosure. Computer instructions or software codes running in the computing devices, computer processors, or programmable logic devices can readily be prepared by practitioners skilled in the software or electronic art based on the teachings of the present disclosure.

All or portions of the methods in accordance to the embodiments may be executed in one or more computing devices including server computers, personal computers, laptop computers, mobile computing devices such as smartphones and tablet computers.

The embodiments include computer storage media having computer instructions or software codes stored therein which can be used to program computers or microprocessors to perform any of the processes of the present invention. The storage media can include, but are not limited to, floppy disks, optical discs, Blu-ray Disc, DVD, CD-ROMs, and magneto-optical disks, ROMs, RAMs, flash memory devices, or any type of media or devices suitable for storing instructions, codes, and/or data.

Each of the functional units in accordance to various embodiments also may be implemented in distributed computing environments and/or Cloud computing environments, wherein the whole or portions of machine instructions are executed in distributed fashion by one or more processing devices interconnected by a communication network, such as an intranet, Wide Area Network (WAN), Local Area Network (LAN), the Internet, and other forms of data transmission medium.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated.

What is claimed is:

1. A method for image-capturing of an internal organ by a miniature imaging device, comprising:
    generating a light at a first light intensity on to a subject area of the internal organ interior wall and capturing an image of the subject area by a miniature imaging device configured under default exposure parameter values;
    computing a second light intensity and optimized exposure parameter values based on brightness of the captured image, an orientation, a position, and a motion of the miniature imaging device at which the image is captured; and
    generating a light at the second light intensity on to the subject area and recapturing the image of the subject area by the miniature imaging device configured under the optimized exposure parameter values;
    wherein the computation of the second light intensity and the optimized exposure parameter values comprising an auto-exposure (AE) process performed by an AE engine module, the AE process comprising:
        dividing the image into a plurality of image zones;
        calculating a first average luma of the image zones;
        determining if the image is overexposed, wherein the image is overexposed if the first average luma is larger than a sum of a target luma and a tolerance value;
        determining if the image is underexposed, wherein the image is underexposed if the first average luma is smaller than the target luma minus the tolerance value;
        if the image is determined to be underexposed:
            calculating a second average luma of two or more image zones with lowest luma values among all the image zones;
            if the miniature imaging device camera is facing away from the internal organ interior wall at a pitch angle and the miniature imaging device is spinning, or if the miniature imaging device camera is facing the internal organ interior wall and the miniature imaging device is moving away from the internal organ interior wall, then setting the optimized exposure parameter values to a first set of predefined exposure parameter values and the second light intensity to the first light intensity increased by a delta luma;
            else if the miniature imaging device is stationary, then setting the optimized exposure parameter values to the default exposure parameter values and the second light intensity to the first light intensity increased by a delta luma;
        if the image is determined to be overexposed:
            calculating a second average luma of two or more image zones with highest luma values among all the image zones;
            if the miniature imaging device camera is closely facing toward the organ interior wall and the miniature imaging device is moving sideways along the organ interior wall, setting the second light intensity to a predefined light intensity and the exposure parameter to predefined exposure parameter values tuned for overexposure condition;
            else if the miniature imaging device camera is facing away from the internal organ interior wall at a pitch angle and the miniature imaging device is spinning in circle, or if with the camera facing the internal organ interior wall the miniature imaging device is moving toward the internal organ interior wall, then setting the optimized exposure parameters to a second set of predefined exposure parameter values and the second light to the first light intensity decreased by the delta luma;
            else if the miniature imaging device is stationary, then setting the optimized exposure parameter values to the default exposure parameter values and the second light intensity to the first light intensity decreased by the delta luma;
        wherein the delta luma being a difference between a target luma and the second average luma.

2. The method of claim 1, wherein the second light intensity and the optimized exposure parameter values are computed by an ex vivo processing unit in wireless data communication with the miniature imaging device, and the second light intensity and the optimized derived parameter values are transmitted to the miniature imaging device.

3. The method of claim 1, wherein the AE process further comprising assigning a weighting factor for each luma of each of the image zones;
wherein the average luma is an average luma of weighted lumas of the image zones.

4. The method of claim 1, wherein the image frames are constructed as i×j uniform squares, and wherein i=4 to 6, and j=4 to 6.

5. The method of claim 1, wherein the AE process further comprising:
if the image is determined to be neither overexposed nor underexposed, then determining if a region of interest (ROI) is overexposed, comprising:
grouping one or more of the image zones according to their lumas into the ROI;
computing a group luma of the ROI image zones;
determining if the image is overexposed, wherein the image is overexposed if the group luma is larger than the sum of the target luma and the tolerance value.

6. The method of claim 5, wherein the ROI comprises bright image zones in one of a bright left transitioning to dark right pattern, a bright right transitioning to dark left pattern, a bright top transitioning to dark bottom pattern, a bright bottom transitioning to dark top pattern, a bright corner transitioning to dark opposite corner pattern, or a center bright center transitioning to dark perimeter pattern in the image.

7. The method of claim 1, wherein the position and the motion of the miniature imaging device are obtained from control data of an ex-vivo magnetic inducing module in magnetic manipulation of the miniature imaging device.

8. The method of claim 1, wherein the orientation of the miniature imaging device is obtained from inertial data generated by an inertial measurement unit (IMU) in the miniature imaging device.

9. The method of claim 1, wherein the internal organ is one or gastrointestinal tract selected from esophagus, stomach, duodenum, small intestine, large intestine, rectum, or colon.

10. An apparatus for image-capturing of an internal organ, comprising:
a miniature imaging device configured to:
generate a light at a first light intensity on to a subject area of the internal organ interior wall and capture an image of the subject area by a miniature imaging device configured under default exposure parameter values; and
generate a light at a second light intensity on to the subject area and recapture the image of the subject area with the miniature imaging device configured under optimized exposure parameter values; and
an auto-exposure (AE) engine module configured to:
compute a second light intensity and the optimized exposure parameter values based on brightness of the image, an orientation, a position, and a motion of the miniature imaging device at which the image is captured;
wherein the computation of the second light intensity and optimized exposure parameter associated with a second light intensity comprising an auto-exposure (AE) process performed by the AE engine module, the AE process comprising:
dividing the image into a plurality of image zones;
calculating a first average luma of the image zones;
determining if the image is overexposed, wherein the image is overexposed if the first average luma is larger than a sum of a target luma and a tolerance value;
determining if the image is underexposed, wherein the image is underexposed if the first average luma is smaller than the target luma minus the tolerance value;
if the image is determined to be underexposed:
calculating a second average luma of two or more image zones with lowest luma values among all the image zones;
if the miniature imaging device camera is facing away from the internal organ interior wall at a pitch angle and the miniature imaging device is spinning, or if the miniature imaging device camera is facing the internal organ interior wall and the miniature imaging device is moving away from the internal organ interior wall, then setting the optimized exposure parameter values to a first set of predefined exposure parameter values and the second light intensity to the first light intensity increased by a delta luma;
else if the miniature imaging device is stationary, then setting the optimized exposure parameter values to the default exposure parameter values and the second light intensity to the first light intensity increased by a delta luma;
if the image is determined to be overexposed:
calculating a second average luma of two or more image zones with highest luma values among all the image zones;
if the miniature imaging device camera is closely facing toward the organ interior wall and the miniature imaging device is moving sideways along the organ interior wall, setting the second light intensity to a predefined light intensity and the exposure parameter to predefined exposure parameter values tuned for overexposure condition;
else if the miniature imaging device camera is facing away from the internal organ interior wall at a pitch angle and the miniature imaging device is spinning in circle, or if with the camera facing the internal organ interior wall the miniature imaging device is moving toward the internal organ interior wall, then setting the optimized exposure parameters to a second set of predefined exposure parameter values and the second light to the first light intensity decreased by the delta luma;
else if the miniature imaging device is stationary, then setting the optimized exposure parameter values to the default exposure parameter values and the second light intensity to the first light intensity decreased by the delta luma;
wherein the delta luma being a difference between a target luma and the second average luma.

11. The apparatus of claim 10, wherein the AE engine module is in an ex vivo processing unit in wireless data communication with the miniature imaging device, and the second light intensity and the optimized derived parameter values are transmitted to the miniature imaging device.

12. The apparatus of claim 10, wherein the AE process further comprising assigning a weighting factor for each luma of each of the image zones;

wherein the average luma is an average luma of weighted lumas of the image zones.

13. The apparatus of claim 10, wherein the image frames are constructed as i×j uniform squares, and wherein i=4 to 6, and j=4 to 6.

14. The apparatus of claim 10, wherein the AE process further comprising:
if the image is determined to be neither overexposed nor underexposed, then determining if a region of interest (ROI) is overexposed, comprising:
grouping one or more of the image zones according to their lumas into the ROI;
computing a group luma of the ROI image zones;
determining if the image is overexposed, wherein the image is overexposed if the group luma is larger than the sum of the target luma and the tolerance value.

15. The apparatus of claim 14, wherein the ROI comprises bright image zones in one of a bright left transitioning to dark right pattern, a bright right transitioning to dark left pattern, a bright top transitioning to dark bottom pattern, a bright bottom transitioning to dark top pattern, a bright corner transitioning to dark opposite corner pattern, or a center bright center transitioning to dark perimeter pattern in the image.

16. The apparatus of claim 10, wherein the position and the motion of the miniature imaging device are obtained from control data of an ex-vivo magnetic inducing module in magnetic manipulation of the miniature imaging device.

17. The apparatus of claim 10, wherein the orientation of the miniature imaging device is obtained from inertial data generated by an inertial measurement unit (IMU) in the miniature imaging device.

18. The apparatus of claim 10, wherein the internal organ is one or gastrointestinal tract selected from esophagus, stomach, duodenum, small intestine, large intestine, rectum, or colon.

* * * * *